(12) United States Patent
Lluel et al.

(10) Patent No.: US 9,511,061 B2
(45) Date of Patent: Dec. 6, 2016

(54) INCONTINENCE TREATMENT METHODS

(75) Inventors: Philippe Lluel, Ramonville Saint Agne (FR); Stefano Palea, Toulouse (FR)

(73) Assignee: IXALTIS, Toulouse (FR)

( * ) Notice: Subject to any disclaimer, the term of this patent is extended or adjusted under 35 U.S.C. 154(b) by 1548 days.

(21) Appl. No.: 12/158,444

(22) PCT Filed: Dec. 20, 2006

(86) PCT No.: PCT/FR2006/051396
§ 371 (c)(1),
(2), (4) Date: Jun. 20, 2008

(87) PCT Pub. No.: WO2007/074291
PCT Pub. Date: Jul. 5, 2007

(65) Prior Publication Data
US 2008/0305162 A1  Dec. 11, 2008

(30) Foreign Application Priority Data
Dec. 22, 2005 (FR) ................................. 05 13163

(51) Int. Cl.
*A61K 31/445* (2006.01)

(52) U.S. Cl.
CPC .................... *A61K 31/445* (2013.01)

(58) Field of Classification Search
CPC ................ A61K 31/445; A61K 31/4465
See application file for complete search history.

(56) References Cited

FOREIGN PATENT DOCUMENTS

| EP | 0077427 | | 4/1983 |
| EP | 0467365 | A2 * | 1/1992 |
| EP | 1199069 | | 4/2002 |
| WO | WO 03/063873 | A1 * | 8/2003 |
| WO | WO 2004/089288 | A2 * | 10/2004 |

OTHER PUBLICATIONS

Vippagunta et al. 2001, Advanced Drug Delivery Reviews, vol. 48, pp. 3-26.*
Lucchelli et al. 1995, "The interaction of antidepressant drugs with central and peripheral (enteric) 5-HT3 and 5-HT4 receptors." British Journal of Pharmacology, vol. 114, pp. 1017-1025.*
Bhattacharya et al. The Journal of Neuroscience, 2004, 24(24), pp. 5537-5548.*
Doi, T. et al. "Effects of TAK-637, a tachykinin receptor antagonist, on lower urinary tract function in the guinea pig" *European Journal of Pharmacology*, 1999, pp. 297-303, vol. 383.
Rao, S.S. et al. "Diagnosis and Management of Fecal Incontinence" *Am. J. Gastroenterology*, 2004, pp. 1585-1604, vol. 99.
Corsi, M. et al. "Pharmacological analysis of 5-hydroxytryptamine effects on electrically stimulated human isolated urinary bladder" *British Journal of Pharmacology*, 1991, pp. 719-725, vol. 104.
Espey, M. J. et al. "Serotonergic modulation of cat bladder function before and after spinal transection" European Journal of Pharmacology, 1995, pp. 173-177, vol. 287.
Robertson, D. W. et al. "Zatosetron, a Potent, Selective, and Long-Acting 5HT_3 Receptor Antagonist: Synthesis and Structure-Activity Relationships" *Journal of Medicinal Chemistry*, 1992, pp. 310-319, vol. 35, No. 2.
Testa, R. et al. "Effect of different 5-hydroxytryptamine receptor subtype antagonists on the micturition reflex in rats" *BJU International*, 2001, pp. 256-264, vol. 87.
Nitti, M. "Duloxetine: A New Pharmacologic Therapy for Stress Urinary Incontinence" *Reviews in Urology*, 2004, pp. S48-S55, vol. 6, Suppl. 3.

* cited by examiner

*Primary Examiner* — Kara R McMillian
(74) *Attorney, Agent, or Firm* — Saliwanchik, Lloyd & Eisenschenk

(57) ABSTRACT

The invention relates to the fields of pharmaceutical chemistry and pharmacological treatments. More specifically, the invention relates to compositions and methods for the treatment of incontinence, voiding disorders associated with lower urinary tract dysfunctions and/or the urethro-vesical and anal sphincteral disorders. The invention can be used, for example, for the treatment of pollakiuria, urinary urgency, nocturia or enuresis, true faecal incontinence, functional faecal incontinence (FFI), passive faecal incontinence, faecal urgency and/or faecal seepage. The invention is suitable for preventive or curative use with all mammals, particularly humans.

13 Claims, 3 Drawing Sheets

INCONTINENCE TREATMENT METHODS

Figure 1:
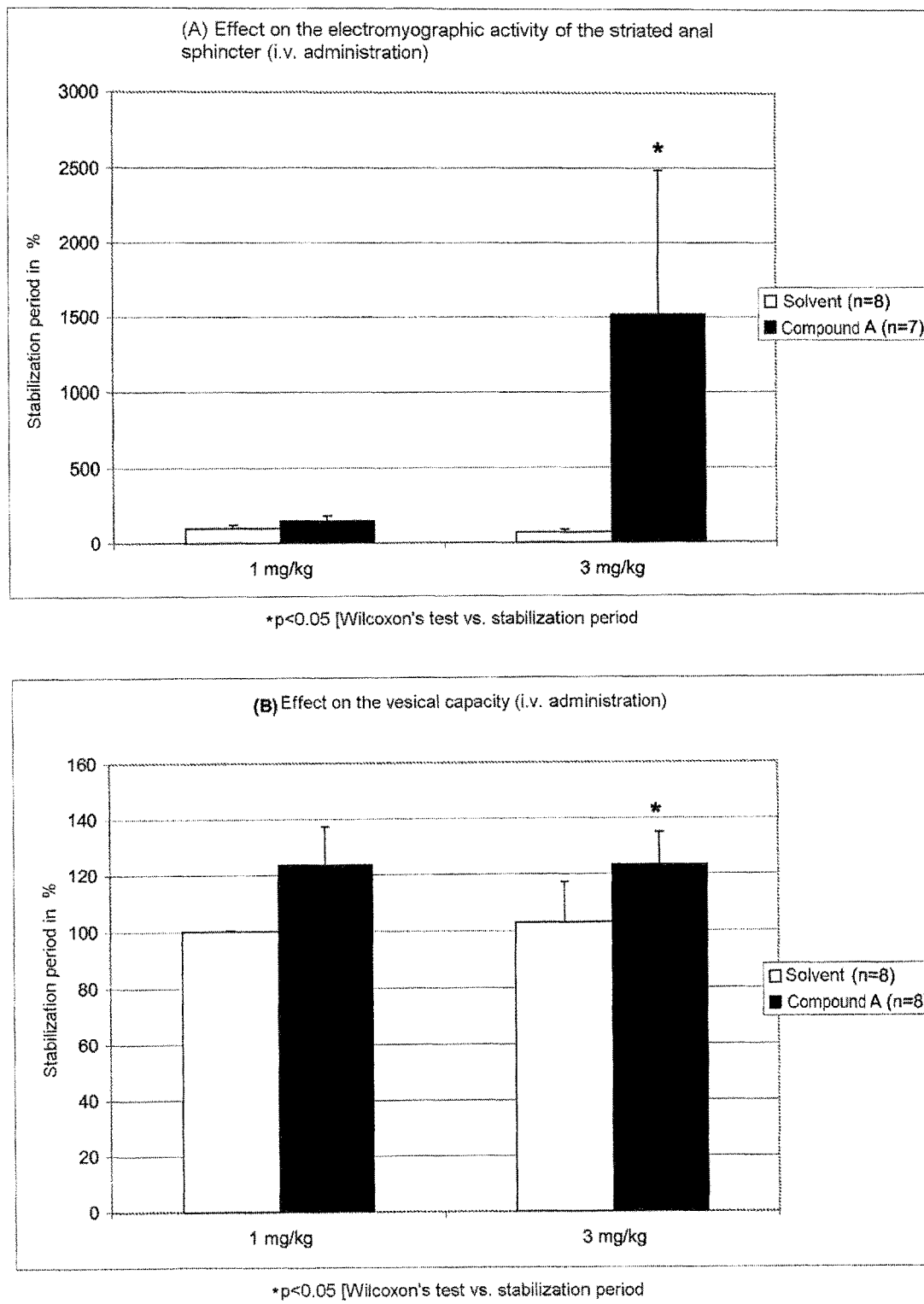

The present invention relates to the fields of pharmaceutical chemistry and pharmacological treatments. More particularly, it relates to compositions and methods for treating incontinences, micturitional disorders associated with lower urinary tract dysfunctions and/or urethra-vesical and anal sphincteral disorders. The invention may be notably used for treating pollakiuria, urinary urge or urgency, nocturia or enuresis, faecal urgency and faecal seepage, and may be applied to all mammals in particular humans, for preventive or curative use.

The lower urinary tract dedicated to storing urine (continence) and to its removal (micturition) consists of ureters, the bladder, urinary sphincters and the urethra. In men, the prostate is associated with it because of frequent micturitional repercussions which infections, inflammations or prostatic hyperplasias may have.

Urinary incontinence is defined by involuntary loss of urine and results from a deficiency in controlling the bladder and/or the muscles of the urinary sphincters. Apart from micturition where they are voluntarily released, the urinary sphincters are sufficient contracted in order to contain the pressure exerted by the vesical muscles. Urinary incontinence occurs when the vesical pressure is too strong or when the contraction of the urinary sphincters is too weak for containing normal intra-vesical pressure.

Urinary incontinence exists in different forms: stress incontinence, urgency incontinence, mixed incontinence, overflow incontinence and functional incontinence.

Effort urinary incontinence expresses itself by a loss of urine when pressure is exerted at the abdomen (physical exercise, coughing attack or burst of laughter). This form of incontinence related to a dysfunction of the urinary sphincters and of the urethra is mainly encountered in women.

Urgency urinary incontinence expresses itself by an incapability of containing a strong urge for urinating and results from reduction in the vesical filling capacity (lack of compliance) or from abnormal contraction of the detrusor muscle during the bladder filling phase. It essentially affects elderly subjects. Depending on the cause either neurological or not of the dysfunction of the vesical muscle, two pathologies are distinguished: hyperreflexia of the detrusor muscle and instability of the detrusor muscle. Detrusor hyperreflexia appears during neurological attacks, in particular disseminated sclerosis, spinal cord lesions, peripheral neuropathies or brain tumors. Conversely, instability of the detrusor muscle may have various infectious, inflammatory or hormonal causes and may also be induced by prostatic hypertrophia. 75% of benign hypertrophia cases of the prostate are actually accompanied by vesical hyperactivity (Scrip Reports, September 2000).

In mixed urinary incontinences, symptomatologies of effort and urgency incontinences are combined.

Overflow urinary incontinence occurs by overflow of the bladder following retention of urine. This form of incontinence may occur when the emptying of the bladder is impaired by an obstruction, as in prostatic hypertrophia, or when this emptying is incomplete by lack of contractility of the vesical muscle. This form of incontinence is particularly encountered in diabetic subjects because of peripheral neuropathies which they develop (Scrip Reports, September 2000).

Functional urinary incontinence corresponds to an incapability of retaining one's urine for a cause independent of any neuro-urological perturbation or any dysfunction of the lower urinary tract. 75% of patients suffering from serious neurological affections such as Alzheimer's disease, Parkinson's disease, or sequels of cerebro-vascular strokes are affected by urinary incontinence (Scrip Reports, September 2000).

Urinary incontinence and micturitional disorders affect several hundred million persons worldwide (Scrip Reports, September 2000). If they do not threaten a vital prognosis, theses disorders considerably alter the quality of life for these patients. They may become a real obstacle within the scope of socio-professional life and have significant physiological and psychological repercussions.

In addition to urinary incontinences, other micturitional troubles or disorders are associated with dysfunctions of components of the lower urinary tract, such as pollakiuria (frequent urge to urinate with very little micturition), urinary urge or urgency (urgent need to urinate), nocturia (frequent need to urinate during the night) or enuresis (involuntary micturition or incapability of containing one's urines). These micturitional disorders appear in many pathologies, notably and not exclusively vesical instability, vesical hyperactivity, cystitis, interstitial cystitis, and prostatic diseases (benign hypertrophia of the prostate, prostatic hyperplasia, prostatite and prostadynia). They are also encountered in patients suffering from diabetes, traumas of the spinal cord, or cerebral affections (Alzheimer's disease, Parkinson's disease, tumors or vascular strokes) and may even have an iatrogenic origin (Scrip Reports, September 2000).

Treatments available today are not very numerous. Apart from anticholinergics prescribed in urgency incontinence, $\alpha$-blocking agents used for urinary disorders of patients affected by benign hypertrophia of the prostate and a mixed inhibitor of recapture of norepinephrine and serotonin, duloxetin, recently registered in Europe in stress incontinence, the armamentarium boils down to diverting the use of estrogens, tricyclic anti-depressants and $\alpha_1$-adrenergic agonists. Not very efficient and often badly tolerated, these treatments frequently lead to bad compliance of the patients or even to interruptions of the treatment (Scrip Reports, Sep. 2000).

Faecal incontinence (FI) is defined by an incapability of containing stools (either solid or liquid) after learning cleanliness (Cooper Z. R. et al., 2000). FI is distinguished from anal incontinence (AI) by the nature of the anal losses. While FI only relates to losses of stools (either solid or liquid), AI extends to loss of gases (Macmillan A. K. et al., 2004). "Real faecal incontinence" related to losing control of the anal sphincter is distinguished from functional faecal incontinence (FFI) corresponding to recurrent loss of stools in the absence of any neurological or structural alteration of the control of the anal sphincter (Whitehead W. E. et al., 2006). FFI groups pathologies which may have both an anal origin (hemorrhoids, anal fistula, prolapse of the faecal mucosa) and an intestinal origin (abuse of laxatives, inflammatory or parasitic pathologies of the intestine). Clinically, there are three subtypes of FI: passive faecal incontinence (involuntary loss of stools and without any perceptions), urgency faecal incontinence or faecal urgency (faecal loss in spite of an attempt to contain the faecal bolus) and faecal seepage (faecal leak, although defecation is normal) (Rao S., 2004). Passive FI appears during dysfunction of the internal anal sphincter or during obstruction of the rectum by stools (occurrence of an overflow of liquid stools around the obstacle, caused by constipation) (Kamm M. A., 1998). Urgency faecal incontinence may result from an affection or dysfunction of the external anal sphincter, but it may also be consecutive to an increase in the intestinal pressure, while the sphincter is intact (e.g.: diarrheas of various origins, irritable colon syndrome) (Engel A. F. et al., 1995).

Faecal incontinence is a complex and multifactorial disorder, the origins of which may be very diverse. Affections of the sphincter (from weakness to failure), neuropathies of the pudendal nerve, anorectal sensitive alterations, alterations of rectal compliance, incomplete defecation, are as many possible causes for occurrence of FI; these affections may themselves have various origins (anatomic, local or systemic origins). Moreover, it is frequent that FI has multiple causes (Bharucha A. E., 2003 and Cooper Z. R. et al., 2000).

Currently, it seems to be recognized that prevalence of FI would be of the order of 2% for the general population, of about 7% for autonomous persons of more than 65 years of age and of 25-33% for institutionalized or hospitalized elderly persons (with, for this population, very frequent association with urinary incontinence) (Kamm M. A., 1998).

Recent studies have shown frequent association between urinary incontinence and faecal incontinence. In the United States, in a mixed population of more than 50 years of age, prevalence of dual incontinence is 5.9% (men) and 9.4% (women) (Roberts R. O. et al., 1999). Similar prevalences (8.4% and 8.7%) were reported for women in Europe (Griffiths A. N. et al., 2006 and Lacima G. et al., 2002). Very frequent association of urinary and faecal incontinences may be explained by similarities existing in the operation of the urethral sphincter and of the anal sphincter (Leroi and Le Normand, 2005). Detection in animals of crossed reflexes between the bladder, the urethra, the ano-rectal complex and the pelvic diaphragm has also been put forward for explaining at least partly, co-morbidity of both of these incontinences (Kappor et al., 2005).

Beside protective diapers, diet measures, rehabilitation techniques (biofeedback, pelvic rehabilitation), various medical devices and surgery (sphincter repair, muscular transposition, artificial sphincter, stimulation of the sacral nerve, colostomy, etc.), pharmacological treatments proposed or studied in the treatment of FI are not very numerous to this day. In most cases, these are non-specific treatments intended to act on the suspected cause of incontinence, i.e. diarrhea or constipation (Rao S., 2004, Bharucha A. E., 2003).

Confronted with the considerable number of patients affected by urinary incontinence, micturitional disorder, faecal or anal incontinence and/or urethro-vesical and anal sphincteral disorders and with the unsuitability of available treatments, there is an obvious need for efficient treatments without any secondary effects.

The present invention now proposes novel efficient methods for treating these pathologies. Unexpectedly it was observed that certain derivatives of piperidine, the preparation and antidepressive activity of which are revealed in Patent No. EP77427, have a pharmacological effect on the bladder and on the anal and urethral muscular sphincteral system, the dysfunctions of which are involved in urinary, faecal, or anal incontinences. In particular, the examples disclosed in the present application show that unexpectedly, these compounds administered intravenously, increase the vesical capacity and the electromyographic activity of the striated anal sphincter; the latter being notably recognized in the literature as being representative of that of the urethral sphincter (Thor and Muhlhauser, 1999 and Wenzel et al., 2006). Moreover, in vitro, these compounds inhibit in a concentration-dependent way, the contractile response of the electrically stimulated human bladder and inhibit potentialization by serotonin of the neurogenic response of the rat bladder (contractile response to electric stimulation).

An object of the invention therefore lies in the use, for the manufacture of a medicament for treating incontinences, micturitional disorders associated with dysfunctions of the lower urinary tract and/or urethro-vesical and anal sphincteral disorders, of a compound of formula (I)

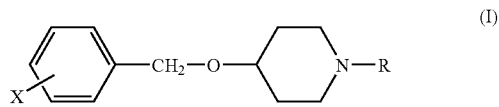

(I)

wherein

R represents a hydrogen atom or a $(C_1-C_4)$-alkyl, hydroxy-$(C_1-C_4)$ alkyl, $(C_1-C_4)$-alkoxycarbonyl or benzyl radical, said radicals being optionally substituted with one or more substituents preferably selected from a halogen atom and a $(C_1-C_4)$-alkoxy, phenethyl or phenyl-3-propyl radical, X represents one or more hydrogen or halogen atoms or radicals selected from $(C_1-C_4)$ alkyl, $(C_1-C_4)$-alkoxy, trifluoromethyl and methylenedioxy, or else X forms with the phenyl ring a naphthyl radical, as well as the pharmaceutically acceptable salts and hydrates thereof.

Another object of the invention relates to a method for treating incontinences, micturitional disorders associated with dysfunctions of the lower urinary tract and/or anal and urethro-vesical sphincteral disorders, comprising the administration to a patient of an efficient amount of a compound of formula (I) as defined above.

Within the context of the invention, the term of "incontinence" designates urinary, faecal or anal incontinences.

Within the context of the invention, the term "$(C_1-C_4)$-alkyl" more preferentially designates methyl, ethyl, propyl or isopropyl and butyl groups. Among the hydroxy-$(C_1-C_4)$-alkyl groups, methoxy and ethoxy groups may be mentioned more specifically. Among the $(C_1-C_4)$-alkoxycarbonyl radicals, $C(O)OCH_3$ and $C(O)OCH_2CH_3$ may notably be mentioned.

In a preferred embodiment, R and X do not represent hydrogen atoms simultaneously. Examples of such compounds are, notably, compounds 1-9 described in EP 077 427.

Particular compounds are those wherein X represents one or more chlorine atoms or forms with the phenyl ring, a naphthyl radical, or further represents three methoxy radicals. Most preferred compounds are those wherein X forms with the phenyl ring, a naphthyl radical.

Another group of preferred compounds is the one wherein R is H.

A most preferred example of compound is 4-[(2-naphthalenyl)-methoxy]-piperidine, of the following formula (compound A):

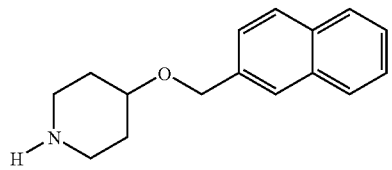 [SMILES: c1ccc2cc(COC3CCNCC3)ccc2c1]

Among pharmaceutically acceptable addition salts, in particular acid salts may be mentioned, such as notably benzoate, mandelate, hydrochloride, citrate and fumarate salts.

The compounds as mentioned above may be produced by various synthesis techniques, known per se to one skilled in the art. In this context, synthesis methods which may be applied for the purposes of the present application, are described in detail, in Patent EP 077 427.

In a particular embodiment of the invention, the compound used has the property of inhibiting the recapture of serotonin (serotonin reuptake). Even more preferentially, this is a selective inhibitor of recapture of serotonin. In the sense of the invention, under the term "selective inhibitor of recapture of serotonin" is meant a compound which, at the doses used, does not have any substantial effect on recapture of norepinephrine or dopamine. Advantageously, an inhibitor of recapture of serotonin is selective when the inhibition ratio $IC50_{NE/HT}$ and/or $IC50_{DA/HT}$ is above 30, 40, 50, 60, 70 or 80, preferably comprised between 50 and 300.

In a particularly advantageous embodiment, the compound further is an agonist, either partial or not, of 5-HT$_{2C}$ receptors and/or an antagonist of 5-HT$_3$ receptors and/or of 5-HT$_4$ receptors and/or of 5-HT$_7$ receptors. The present application indeed shows that compounds having a profile of a selective inhibitor of recapture of serotonin combined with an agonistic activity, either partial or not, of the 5-HT$_{2C}$ receptors and/or an antagonistic activity of the 5-HT$_4$ receptors and/or 5-HT$_7$ receptors produce a particularly advantageous effect on the urethral pressure and on the contractile response of the bladder and limit the risks of vomiting because of their antagonistic activity on the 5-HT$_3$ receptors. The term "agonist of a receptor" designates any compound capable of binding to said receptor and of mimicking the response induced by the natural ligand of said receptor. The term "antagonist of a receptor" designates any compound capable of binding to the said receptor and of blocking the response induced by the natural ligand of said receptor.

Most particularly preferred compounds are those which have, in combination with one, some or all of the aforementioned properties, a low affinity for dopaminergic receptors D$_2$ (i.e. less by a factor 5, 10, 20 or 30 at least relatively to the affinity for the carrier of serotonin) and/or for adrenergic receptors (i.e. less by a factor 5, 10, 20 or 30 at least relatively to the affinity for the carrier of serotonin) and/or muscarinic receptors (i.e. less by a factor 5, 10, 20 or 30 at least relatively to the affinity for the carrier of serotonin). Indeed, with this selectivity, compounds are made available which do not induce nauseas or cardiovascular (arterial hypertension) and anticholinergic (xerostomy) secondary effects frequently encountered with treatments presently available.

Thus, a particular object of the invention also lies in the use, for the manufacture of a medicament for treating incontinences, micturitional disorders associated with dysfunctions of the lower urinary tract, and/or anal and urethro-vesical, sphincteral disorders, of a compound which is a selective inhibitor of recapture of serotonin, an agonist, either partial or not, of 5-HT$_{2C}$ receptors and/or an antagonist of 5-HT$_3$ receptors and/or of 5-HT$_4$ receptors and/or of 5-HT$_7$ receptors and having low affinity for dopaminergic receptors D$_2$, adrenergic receptors and muscarinic receptors.

A specific example of such a compound is 4-[(2-naphthalenyl)-methoxy]-piperidine. The applicants have indeed shown that this compound had clear selectivity on recapture of serotonine (5-HT) as compared with that of norepinephrine (NE) ($IC_{50\ NF/HT}$ ratio=89), (Scatton, 1988), and very low affinity for adrenergic receptors [$\alpha_1$($IC_{50}$=40 µM, $\alpha_2$ ($IC_{50}$=70 µM) et β ($IC_{50}$=100 µM] and for muscarinic receptors ($IC_{50}$=99 µM). Because of this selectivity, this compound should not cause cardiovascular (arterial hypertension) and anticholinergic (xerostomy) secondary effects frequently encountered with the treatments presently available. Furthermore, the clear selectivity of 4-[(2-naphthalenyl)-methoxy]-piperidine on recapture of serotonin as compared with that for dopamine (DA) ($IC_{50\ DA/HT}$ ratio=188), (Scatton, 1988), its antagonistic activity on the 5-HT$_3$ receptor and its antiemetic properties in animals (Angel, 1993) should reduce or even suppress vomiting which frequently accompanies treatment by duloxetin. In addition, studies of binding on cloned human receptors have shown that 4-[(2-naphthalenyl)-methoxy]-piperidine has significant affinities for the 5-HT$_{2A}$, 5-HT$_{2B}$, 5-HT$_{2C}$, 5-HT$_3$, 5-HT$_{4e}$, and 5-HT$_7$ receptors with $IC_{50}$s comprised between 0.25 µM and 7.2 µM, but low affinity for 5-HT$_{1A}$ and 5-HT$_{5A}$ receptors. It was further shown, for the first time, that this compound is a partial agonist of the 5-HT$_{2C}$ receptor, with an IC of 1.5 µM, which is a particular advantage in the treatment of pathologies involving abnormal activity of the bladder (Steers, 1989, Steers, 1992; Guarneri, 1996; Leysen, 1999). In addition, the unexpected inhibition of potentialization by serotonin of the neurogenic response of the electrically stimulated isolated rat bladder, observed at 10 µM may involve an antagonistic activity on the 5-HT$_7$ receptors (Palea, 2004), which is of interest in treating urgency urinary incontinences and mixed urinary incontinences because of the presence of 5-HT$_7$ receptors in the human bladder (D'Agostino, 2006).

A most particular object of the invention therefore lies in the use of 4-[(2-naphthalenyl)-methoxy]-piperidine, or a salt thereof, for preparing a drug for treating incontinences, micturitional disorders associated with dysfunctions of the lower urinary tract, and/or anal and urethro-vesical, sphincteral disorders.

The invention may notably be used for treating urinary incontinences and micturitional disorders associated with dysfunctions of the lower urinary tract, and notably of pollakiuria, urinary urge or urgency, nocturia or enuresis. These micturitional disorders appear in many pathologies, notably vesical instability, vesical hyperactivity, cystitis, interstitial cystitis and prostatic diseases (benign hypertrophia of the prostate, prostatic hyperplasia, prostatite and prostadynia). They are also encountered in patients suffering from diabetes, traumas of the spinal cord, or cerebral affections (Alzheimer's disease, Parkinson's disease, tumors or vascular strokes) and may even have an iatrogenic origin.

It is also particularly suitable for treating anal and faecal incontinences, and notably real faecal incontinences and functional faecal incontinences (FFI). It is useful both in the treatment of passive faecal incontinences, urgency faecal incontinences, and faecal seepage.

In the sense of the invention, the term "treatment" designates both a curative and preventive treatment. This term encompasses any improvement in the symptoms of the disease or any reduction of outward signs of the considered disorders, and notably a reduction of their frequency, of the trouble or discomfort, of pain, or even total disappearance of the disorders. The treatment may be used alone or in combination with other active ingredients, either simultaneously or separately or sequentially.

The treatment method described in the present invention comprises the administration of a therapeutically effective dose to a patient requiring this type of treatment. The term "therapeutically effective dose" designates a sufficient amount of compound for treating the incontinence or for obtaining either a complete or partial reduction, of at least one of the symptoms selected from pollakiuria, urinary urge, nocturia, enuresis, faecal urgency or faecal seepage, for example.

The effective dose, which may vary, is determined by the physician attending the patient. This effective dose may require adjustment when the compound is administered as a salt, in particular when the latter has a large molecular weight.

The range of effective doses is typically comprised between 0.001 and 1,000 mg/day. The effective dose is formulated in a suitable pharmaceutical preparation, and may be, depending on the need, contained in totality in a daily dose of this preparation or administered by fractions at different hours of the day.

According to the invention, the compounds may be administered through an oral, buccal, sublingual, rectal, vaginal, nasal, transcutaneous, parenteral, intra-vesical, transurethral, or systemic route. The administration route is not a critical element of the invention. As the compound is absorbed at the digestive tract, it is preferentially administered orally, for reasons of convenience, but it may if necessary be administered through any pharmaceutically acceptable route.

The compounds used in the invention may be administered as any of the usual pharmaceutical forms, such as tablets, either coated or not, tablets to be crunched or to be sucked, lozenges, gelatine capsules, soft capsules, solutions, aqueous or oily suspensions, emulsions, injectable solutions, suppositories, syrups, granules, powders, patches, gels, creams, ointments, sprays and aerosols.

These pharmaceutical preparations may be formulated so as to contain a daily dose or a fraction of the daily dose in a dosage unit which may be a solid entity, such as a tablet, or a suitable volume of a solid preparation, either liquid or semi-solid. Depending on the need in terms of delay and time of action, the compound may be administered in a controlled-release formulation (delayed, extended, programmed, pulsatile form).

The activity of the compound does not depend on the composition of the formulation in which it is administered, or on the concentration of the compound in these formulations.

The formulations are prepared with pharmaceutically acceptable excipients, selected according to usual pharmaceutical practices, depending on the desired pharmaceutical form. In the case of solid oral pharmaceutical formulations, these excipients notably include binding agents (hydroxypropylcellulose, polyvinylpyrrolidone, starch), inert diluents (lactose, calcium carbonate, microcrystalline cellulose), lubricants (silica, talc, magnesium stearate, stearic acid), disintegration agents (starch sodium glycolate, alginic acid), wetting agents (sodium laurylsulphate) and/or coating or film-forming agents, either aqueous or non-aqueous.

The liquid preparations may use aqueous carriers (water, water-alcohol mixtures, saline, buffers) or non-aqueous carriers (propylene glycol, polyethylene glycol, injectable organic esters such as ethyl oleate). They may contain suspension agents (sorbitol, methyl cellulose), emulsifiers (gums, lecithins), preservatives, flavoring agents, dyes, and/or sweeteners.

Topical preparations may contain absorption promoters.

Thus, another object of the invention relates to any pharmaceutical composition comprising a compound as defined hereinbefore, as well as any carrier or excipient suitable for use in the treatment of incontinences, micturitional disorders associated with dysfunctions of the lower urinary tract, and/or anal and urethro-vesical sphincteral disorders.

Other aspects and advantages of the invention will be disclosed in the following examples which should be considered as illustrative and non-limiting.

LEGEND TO THE FIGURES

FIG. 1: Increase in the activity of the striated anal sphincter (A) and in the vesical capacity (B) by the compound A in anaesthetized female rabbits under conditions of vesical irritation induced by local perfusion of diluted acetic acid.

Figure 2:
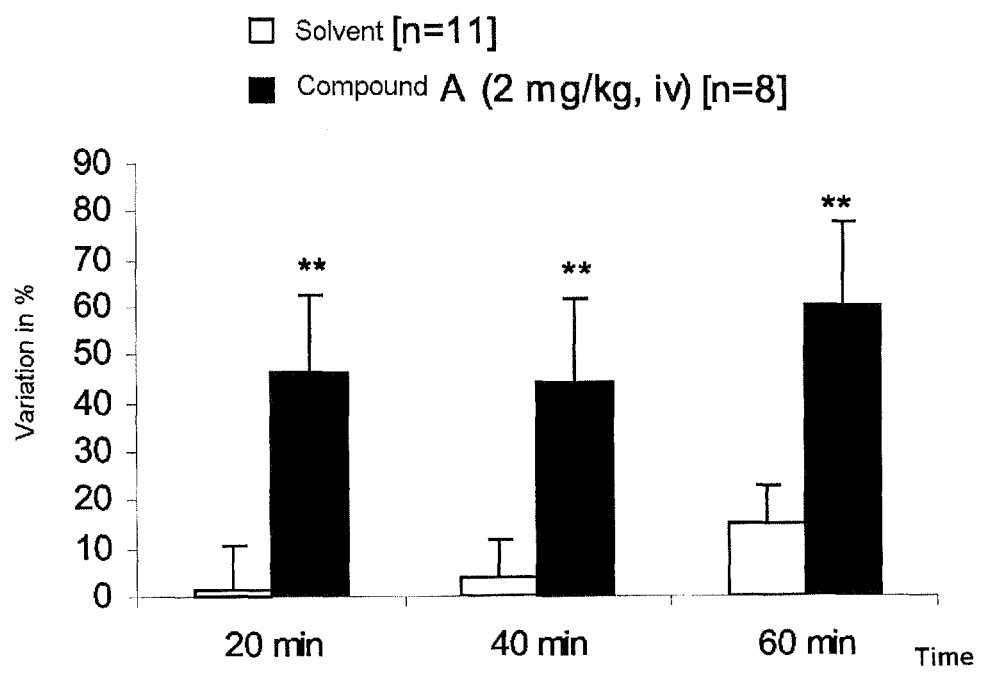

FIG. 2: Increase in the vesical capacity by the compound A in anaesthetized female rats under conditions of vesical irritation induced by local perfusion of diluted acetic acid.

Figure 3:
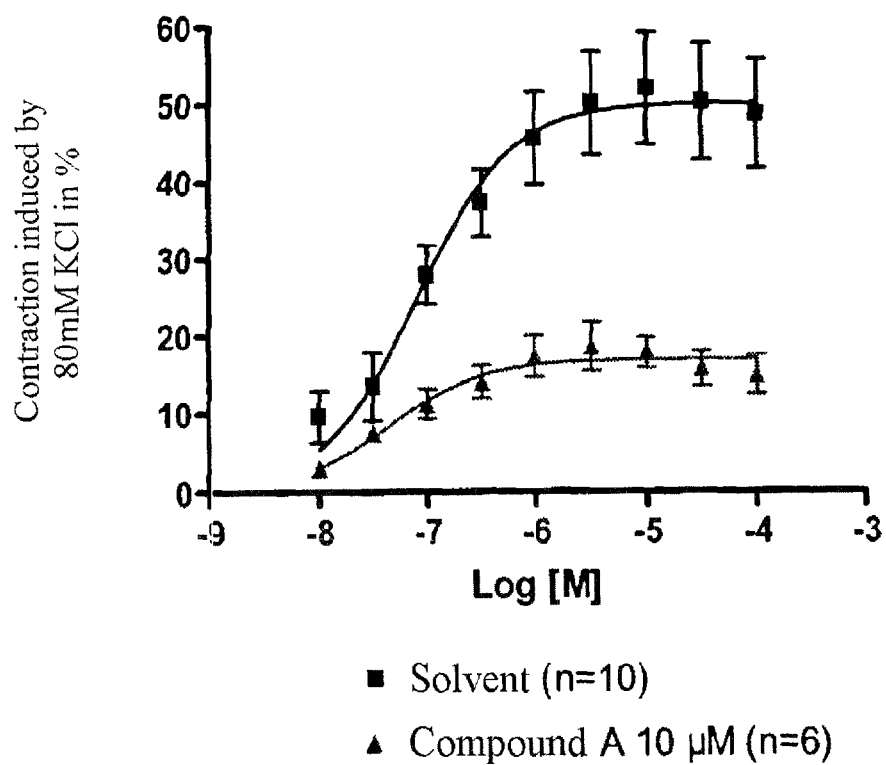

FIG. 3: Antagonism by the compound A of the potentialization of the neurogenic response induced by 5-HT in the isolated rat bladder.

EXAMPLES

Example 1

Effect of Compounds of Formula (I) on the Activity of the Striated Anal Sphincter and on the Vesical Capacity In Vivo in Anaesthetized Female Rabbits Under Conditions of Vesical Irritation Induced by Intra-Vesical Perfusion of Diluted Acetic Acid The effect of 4-[(2-naphthalenyl)-methoxy]-piperidine (compound A) and of its solvent (NaCl 0.9%) on the electromyographic activity of the striated anal sphincter (EMG-SAS), used as a marker of the activity of the urethral sphincter, and on the vesical capacity (VC) was studied in vivo in anaesthetized female rabbits under conditions of vesical irritation induced by intra-vesical perfusion of diluted acetic acid (Perez Martinez et al., 2006 and Haab et al., 2006). The activity of the striated anal sphincter (SAS) is actually recognized in the literature as being notably representative of that of the urethral sphincter (Thor and Muhlhauser, 1999 and Wenzel and al., 2006). 16 New Zealander female white rabbits (2.5-3.5 kg) anaesthetized by intramuscular injection of a mixture of ketamin (25 mg/kg) and sylazin (10 mg/kg), were subject to cystostomy. After laparotomy by median incision, a catheter was introduced at the dome of the bladder and held in place by a purse suture. A multiperforable plug was placed at the end of the catheter, and then the catheter was internalized subcutaneously and attached at the abdomen with a silk ligature. 3 days after cystotomy, cystomanometry was performed on animals anaesthetized with halothane (2-3%). A T-tube was connected at the multiperformable plug, and then connected to a pressure sensor (Letica, PanLab) and to a micro-pump allowing perfusion of the bladder (Razel 99, Scientific Instruments). Diluted acetic acid (0.5%), held at room temperature, was perfused into the bladder (1.4 mL/h), in order to produce successive micturitions under vesical irritation conditions. The micturitional profile was continuously recorded by means of a data acquisition system (PowerLab 4/25, PanLab) and the different urodynamic parameters, including vesical capacity (VC), were determined. Moreover, two electrodes were introduced at the striated anal sphincter in order to measure its electromyographic activity (EMG). The electric signal, amplified and filtered (bandwidth 1 Hz-5 kHz) was continuously recorded by means of the data acquisition system. EMG-SAS was measured during the phase for filling the bladder, in order to get rid of the parasitics related to perineal movements occurring during micturition.

A catheter was implanted at the vein of the ear in order to allow administration of compound A or of its solvent (NaCl 0.9%) in a volume of 1 mL. The animals were divided into two groups receiving the compound A or its solvent. During a stabilization period (SP) of at least 60 minutes, during which the bladder was perfused, in order to induce regular micturitional cycles, two consecutive doses (1 and 3 mg/kg of compound A or of solvent were administered intravenously, at intervals of 40 minutes. For each of the tested doses, the effects of the compound A and of its solvent on EMG-SAS and on VC were expressed as a percentage of the stabilization period (mean±standard error of mean). During the stabilization period, the parameters obtained in both experimental groups (compound A and solvent) were the same (p>0.05; Kruskal-Wallis test): for EMG-SAS, 1.76±1.04 (n=8) and 1.41±0.59 activity peaks/minute (n=8), for the compound A and its solvent and for VC, respectively, 21.63±4.92 (n=8) and 18.31±2.90 mL (n=8), for the compound A and its solvent respectively. While at the dose of 1 mg/kg, the compound A did not induce any significant effect on the measured parameters, it produced at the dose of 3 mg/kg a significant increase in EMG-SAS [1,521.90±966.61% (n=7), p=0.018 (Wilcoxon's test)] and VC [123.29±11.62% (n=8), p-0.035 (Wilcoxon's test)] relatively to the stabilization period (see compound A group in FIGS. 1 (A) and 1 (B)). Tested under same conditions, the solvent did not cause any significant increase in VC and EMG-SAS. While no significant difference (p>0.05; Wilcoxon's test) was observed on VS ($1^{st}$ and $2^{nd}$ administration) and on EMG-SAS ($1^{st}$ administration), the second solvent administration induced a reduction in EMG-SAS [−69.59±18.74% (n=8); p=0.035 (Wilcoxon's test)] (see solvent group in FIGS. 1 (A) and 1 (B)).

Example 2

Effect of Compounds of Formula (I) on the Vesical Capacity In Vivo in Anaesthetized Female Rats Under Vesical Irritation Conditions Induced by Intra-Vesical Perfusion of Diluted Acetic Acid The effect of 4-[(2-naphthalenyl)-methoxy]-piperidine (compound A) and of its solvent (NaCl 0.9%) was studied in vivo on a model of vesical hyperactivity induced in female rats by an intra-vesical perfusion of diluted acetic acid (Chuang et al., 2004). 19 female Wistar rats (200-280 g) were anaesthetized with an intra-peritoneal injection of urethane (1.2 g/kg). After laparotomy, a bursa was formed at the dome of the bladder, and then a catheter was introduced and ligatured at this bursa. A catheter was implanted at the jugular vein in order to allow administration of the compound A or its solvent. Cystomanometry was performed on the animals placed beforehand on a heating plate, in order to maintain their body temperature around 37° C. A 3-way valve was positioned at the end of the vesical catheter and then connected to a pump allowing perfusion of the bladder (Model "11" plus, Harvard Apparatus) and to a pressure sensor (MX 860/866 Novatrans, Medex Medical). Diluted acetic acid (0.3%) held at room temperature was perfused into the bladder (3 mL/h) in order to induce successive micturitions under vesical irritation conditions. The micturitional profile was continuously recorded by means of a data acquisition system (MacLab/8$^e$, AD Instruments) and the different urodynamic parameters, including vesical capacity (VC) were determined. The basal values of the urodynamic parameters were determined after a stabilization period of 10 minutes. The compound A (2 mg/kg) or its solvent were then injected intravenously in a volume of 1 mL administered within 5 minutes by means of a syringe pump (Model A-99, Fisher Bioblock Scientific). The effects of the compound A and of its solvent on VC were evaluated at times, 20, 40 and 60 minutes after administration and expressed as a percentage of variation of the basal value (mean±standard error of mean). In both experimental groups (compound A and solvent), the basal values of VC were the same (p>0.05; analysis of variance): 0.045±0.005 mL and 0.042±0.006 mL for the solvent (n=11) and the compound A (n=8), respectively. The compound A (2 mg/kg, i.v.) produced significant increase in VC [46.25±16.40%, 44.61±17.51% and 60.34±17.8%, at times 20, 40 and 60 minutes following administration, respectively, (p<0.05; analysis of variance)] (see compound A group (n=8) in FIG. 2). Tested under the same conditions, the solvent did not cause any significant change in VC whatever the relevant measurement time (p>0.05; analysis of variance) (see solvent group (n=11) in FIG. 2).

Example 3

Effect of Compounds of Formula I In Vitro on the Electrically Stimulated Human Detrusor Muscle The effect of the compound A and of its solvent (Krebs solution) was tested in vitro on bladder strips taken on two male patients (70 and 62 years old) within the scope of a radical cystectomy because of an urothelial carcinoma. The strips were mounted in baths with isolated organs, containing a Krebs solution, heated to 37° C. and oxygenated with carbogen (95% $O_2$ and 5% $CO_2$). After a 60 minute stabilization period, the viability of the strips was tested by performing a contraction with 80 mM KCl. After 30 minutes of wash-out and stabilization, the strips were submitted to electric field stimulation, in order to cause neurogenic contractions. The electric stimulation parameters used were the following: frequency: 30 Hz, maximum voltage, pulse duration 0.1 ms, 5 second pulse trains every 100 s. After stabilization of the neurogenic response (about 30 minutes after beginning of the electric stimulation), a range of cumulative concentration-response curves for the compound A was obtained between 0.01-100 μM. It was shown that from 10 μM, the compound A inhibits in a concentration-dependent way, the contractile response of the detrusor muscle strips to electric stimulation with inhibition percentages of 20.1±4.7% at 10 μM, 41.7±5.2% at 30 μM and 80.8±6.8% at 100 μM. Tested under the same conditions, the solvent of the compound A has an inhibiting effect of the order of 10% on the contractions of the detrusor muscle. These results show that compound A reduces the cholinergic contractile response of the bladder and may thereby be useful in treating urgency urinary incontinence in which there exists an increase in vesical contractions.

Example 4

Binding Tests on Human Serotoninergic Receptors

The affinity of the compound A was evaluated in vitro on 8 cloned human serotoninergic receptors by measuring the specific binding of the ligands to the corresponding receptors according to methods adapted from Mulheron (1994), Bryant (1996), Choi (1994), Hope (1996), Mialet (2000), Rees (1994) and Shen (1993). The $IC_{50}$s and $K_i$s determined for the receptors for which the compound A showed significant affinity, are summarized in Table 1.

TABLE 1

$IC_{50}$s and $K_i$ s of compound A

| Receptor (site) | Compound A | |
|---|---|---|
| | $IC_{50}$ (M) | $K_i$ (M) |
| $5\text{-}HT_{2A}$ (agonist) | $1.0 \cdot 10^{-6}$ | $6.2 \cdot 10^{-7}$ |
| $5\text{-}HT_{2B}$ (agonist) | $1.0 \cdot 10^{-6}$ | $9.8 \cdot 10^{-7}$ |
| $5\text{-}HT_{2C}$ (agonist) | $2.5 \cdot 10^{-7}$ | $2.0 \cdot 10^{-7}$ |
| $5\text{-}HT_3$ | $1.4 \cdot 10^{-6}$ | $7.2 \cdot 10^{-7}$ |
| $5\text{-}HT_{4e}$ | $4.7 \cdot 10^{-6}$ | $1.6 \cdot 10^{-6}$ |
| $5\text{-}HT_7$ | $7.2 \cdot 10^{-6}$ | $2.6 \cdot 10^{-6}$ |

$IC_{50}$: concentration causing half of the inhibition of the specific binding of the control
Ki: inhibition constant (Cheng Prusoff equation)

The compound A did not show any significant affinity for the $5\text{-}HT_{1A}$ and $5\text{-}HT_{5A}$ receptors (inhibition of the specific binding of the control equal to 14% and 1%, respectively).

Example 5

Cellular Functional Test on the Cloned Human Receptor $5\text{-}HT_{2C}$

The agonistic and antagonistic activities of the compound A were evaluated in vitro on the human $5\text{-}HT_{2C}$ receptor expressed in Chinese hamster ovarian cells (CHO cells) in a range of concentrations comprised between 1 nM and 100 μM by quantitation of the binding of the specific ligand of the receptor, [$^{35}$S]GTPγS, according to a method adapted from Adlersberg (2000) and from Cussac (2002). Without any significant antagonistic activity between 1 nM and 1 μM, the compound A exhibited very low antagonistic activity (18%) at 10 μM. Moreover, with an agonistic activity reaching a limit between 44% and 42% for concentrations comprised between $3.10^{-5}$ M and $10^{-4}$ M, the compound A is a partial agonist for the $5\text{-}HT_{2C}$ receptor for which it has an $IC_{50}$ of 1.5 μM.

Example 6

Antagonistic Functional Test on the $5\text{-}HT_7$ Receptor in Isolated Rat Bladder The effect of the compound A and of its solvent (Krebs solution) on the potentialization by serotonin of the neurogenic response of isolated rat bladder was studied in vitro. Strips of detrusor muscle taken from Wistar female rats (250-300 grams) were mounted in baths with isolated organs, containing a Krebs solution, heated to 37° C. and oxygenated with carbogen (95% $O_2$ and 5% $CO_2$). After a 60 minute stabilization period, contraction with 80 mM KCl was achieved. After 30 minutes of wash-out and stabilization, the strips were submitted to electric field stimulation, in order to cause neurogenic contractions. The electric stimulation parameters used were the following: frequency: 5 Hz, maximal voltage, pulse duration 0.3 ms, 10 second pulse trains every 60 s. The compound A and its solvent are incubated for 60 minutes, 30 minutes without electric stimulation and 30 minutes during the phase for stabilizing the neurogenic response. After stabilization, a 5-HT cumulative concentration-response curve range was achieved between 0.01-100 μM. It was shown that 5-HT potentializes in a concentration-dependent way, the neurogenic response of the rat detrusor muscle, with a maximum response of 52.7±7.3% of the reference contraction induced by 80 mM KCl (see FIG. 3, solvent curve (n=10)). After incubation in the presence of 10 μM of compound A, the maximum response of 5-HT only attains 18.7±3.2% of the reference contraction induced by 80 mM KCL (see FIG. 3, compound A curve (n=6)). At 10 μM, the compound A antagonizes in a noncompetitive way, the response to 5-HT on the neurogenic contraction of the isolated rat bladder; this action may be mediated by the $5\text{-}HT_7$ receptor (Palea, 2004).

Example 7

Antagonistic Functional Test on the $5\text{-}HT_4$ Receptor in the Isolated Human Bladder Strips of human detrusor muscle taken on patients having undergone radical cystectomy because of a carcinoma, are mounted in baths with isolated organs, containing a Krebs solution, heated to 37° C. and oxygenated with carbogen (95% $O_2$ and 5% $CO_2$). After 60 minutes of stabilization, contraction with 80 mM KCl is carried out. After 30 minutes of wash-out and stabilization, the strips of detrusor muscle are subject to electric field stimulation in order to cause neurogenic contractions. The stimulation parameters are the following: frequency: 10 Hz, maximal voltage, pulse duration 0.1 ms, 5 second pulse trains every 60 s. The compound A and its solvent (Krebs solution) are incubated for 60 minutes, 30 minutes without electric stimulation and 30 minutes during the phase for stabilizing the neurogenic response. After stabilization, a 5-HT cumulative concentration-response curve range is obtained between 0.01-10 μM.

Example 8

Formulations of Compound of the Invention

This example provides various types of compound formulation according to the invention, suitable for the described therapeutic use.

| Gelatine capsules dosed with 1.25 mg (base) | |
|---|---|
| Compound A benzoate | 1.875 mg (1.25 mg-base) |
| Microcrystalline cellulose | 139.575 mg |
| Starch sodium glycolate | 7.5 mg |
| Magnesium stearate | 0.75 mg |
| Colloidal silica | 0.3 mg |
| | for a gelatine capsule of 150 mg. |

| Gelatine capsules dosed with 2.5 mg (base) | |
|---|---|
| Compound A benzoate | 3.75 (2.5 mg-base) |
| Microcrystalline cellulose | 279.15 mg |
| Starch sodium glycolate | 15 mg |
| Magnesium stearate | 1.5 mg |
| Colloidal silica | 0.6 mg |
| | for a gelatine capsule of 300 mg |

| Gelatine capsules dosed with 5 mg (base) | |
|---|---|
| Compound A benzoate | 7.5 mg (5 mg-base) |
| Microcrystalline cellulose | 136.5 mg |

-continued

| Gelatine capsules dosed with 5 mg (base) | |
|---|---|
| Starch sodium glycolate | 4.5 mg |
| Magnesium stearate | 1.5 mg |
| | for a gelatine capsule of 150 mg. |

Method for Making the Gelatine Capsules

Sieve the compound A, the microcrystalline cellulose, the starch sodium glycolate with a suitable sieve.

Mix the 3 ingredients.

Sieve the magnesium stearate and the colloidal silica.

Lubricate the mixture and fill the gelatine capsules up to the theoretical weight by using an automatic filling machine.

| Gelatine capsules dosed with 10 mg (base) | |
|---|---|
| Compound A benzoate | 15 mg (10 mg-base) |
| Microcrystalline cellulose | 273 mg |
| Sodium carboxymethyl starch | 9 mg |
| Magnesium stearate | 3 mg |
| | for a gelatine capsule of 300 mg. |

| LP tablets dosed with 10 mg (base) | |
|---|---|
| Compound A benzoate | 15 mg (10 mg-base) |
| Methylhydroxylpropylcellulose | 14 mg |
| Di-calcium phosphate | 6.2 mg |
| Sodium microcrystalline cellulose | 36.11 mg |
| Magnesium stearate | 1.05 mg |
| Colloidal silica | 0.14 mg |
| | for a gelatine capsule of 72.5 mg. |

| Gelatine capsules dosed with 10 to 50 mg and with 100 to 200 mg | |
|---|---|
| Compound A benzoate | x mg |
| Microcrystalline cellulose | (94.25 − x)% |
| Starch sodium glycolate | 3% |
| Methylhydroxylpropylcellulose | 2% |
| Colloidal silicon dioxide | 0.25% |
| Magnesium stearate | 0.50% |
| | for a gelatine capsule of 200 mg (dosage from 10 to 50 mg) or for a gelatine capsule of 400 mg (dosage from 100 to 200 mg) |

| Suspension | |
|---|---|
| Compound A benzoate | 50 mg |
| Xanthan gum | 4 mg |
| Microcrystalline cellulose | 40 mg |
| Carboxymethylcellulose | 10 mg |
| Methyl paraben | 10 mg |
| Saccharose | 1.5 g |
| Purified water q.s.p. | 5 mL. |

BIBLIOGRAPHY

Adlersberg M. et al., J. Neurosci. Res., 61: 674-85, 2000
Angel I. et al., Eur. J. Pharmacol., 232: 139-45, 1993
Bharucha A. E., Gastroenterology, 124: 1672-85, 2003
Bryant H. U. et al., Life Sri., 15: 1259-68, 1996
Choi D. S. et al., FEBS Lett, 352: 393-99, 1994
Chuang Y. C. et al., J. Urol., 172: 1529-32, 2004
Cooper Z. R. et coll., Mt Sinai J. Med., 67: 96-105, 2000
Cussac D. et al., Mol. Pharmacol., 62: 578-89, 2002
D'Agostino G. et al., J. Pharmacol. Exp. Ther., 316: 129-35, 2006.
Engel A. F. et coll., Int. J. Colorectal Dis., 10: 152-5, 1995
Griffiths A. N. et coll., J. Obstet. Gynaecol., 26: 442-4, 2006
Guarneri L. et al., Neurourol. Urodyn., 15: 316-17, 1996
Haab F. et al., Neurourol. Urodyn., 25: Abst. N64, 2006
Hope A. G. et al., Brit. J. Pharmacol., 118: 1237-45, 1996
Kamm M. A., BMJ, 316:528-32, 1998
Kapoor D. S. et coll., Int. Urogynecol. J. Pelvic Floor Dysfunct., 16: 321-8, 2005.
Lacima G. et coll., Neurourol. Urodyn., 21: 464-9, 2002
Leroi A. M. et Le Normand L., Prog. Urol., 15: 123-48, 2005
Leysen D. C., I Drugs, 2: 109-20, 1999
Macmillan A. K. et coll., Dis. Colon Rectum, 47: 1341-9, 2004
Mialet J. et al., Brit. J. Pharmacol., 129: 771-81, 2000
Mulheron J. G. et al., J. Biol. Chem., 269: 12954-62, 1994
Palea S. et al., BJU, 94: 1125-31, 2004
Perez Martinez F. C. et al., Pelv. Perineol., 1: NS102-NS103, 2006
Rao S. S., Am. J. Gastroenterol., 99: 1585-604, 2004
Rees S. et al., FEBS Lett., 355: 242-6, 1994
Roberts R. O. et coll., J. Am. Geriatr. Soc, 47: 837-41, 1999.
Scatton B. et al., Drug Dev. Research, 12: 29-40, 1988
Shen Y. et al., J. Biol. Chem., 268: 18200-04, 1993
Steers W. D. et al., Am. J. Physiol., 257: R14441-1449, 1989
Steers W. D. et al., Drug Dev. Res., 27: 361-75, 1992
Thor K. B. and Muhlhauser M. A., Am. J. Physiol., 277: R1002-R1012, 1999
Urinary incontinence: new therapeutic options, Scrip Report, September 2000.
Wenzel B. et al., Neurourol. Urodyn., 25:140-147, 2006
Whitehead W. E. et coll., Gut, 45: 1155-1159, 2006

The invention claimed is:

1. A method for treating stress urinary incontinence or mixed incontinence, the method comprising administering to a subject in need thereof an effective amount of 4-[(2-naphthalenyl)-methoxy]-piperidine, or a pharmaceutically acceptable salt thereof, in an amount between 0.001 and 1000 mg/day.

2. The method according to claim 1, wherein the compound is administered through oral, buccal, sublingual, rectal, vaginal, nasal, transcutaneous, parenteral, intra-vesical, trans-urethral or systemic route.

3. The method according to claim 1, wherein the compound is administered as tablets, lozenges, gelatine capsules, soft capsules, solutions, aqueous or oily suspensions, emulsions, injectable solutions, suppositories, syrups, granules, powders, patches, gels, creams, ointments, sprays or aerosols.

4. The method according to claim 1, wherein said compound has been formulated as a tablet, lozenge, gelatine capsule, soft capsule, suppository, granule, powder or patch.

5. A method for treating stress urinary incontinence or mixed incontinence, the method consisting of administering to a subject in need thereof a formulation comprising an effective amount of 4-[(2-naphthalenyl)-methoxy]-piperidine, or a pharmaceutically acceptable salt thereof, in an amount between 0.001 and 1000 mg/day.

6. The method according to claim 5, wherein the effective amount of 4-[(2-naphthalenyl)-methoxy]-piperidine, or a pharmaceutically acceptable salt thereof, is administered intravenously.

7. The method according to claim 5, wherein the effective amount of 4-[(2-naphthalenyl)-methoxy]-piperidine, or a pharmaceutically acceptable salt thereof, is administered topically in a formulation, said formulation comprising 4-[(2-naphthalenyl)-methoxy]-piperidine, or a pharmaceutically acceptable salt thereof, in combination with an absorption promoter.

8. The method according to claim 1, wherein the effective amount of 4[(2-naphthalenyl)-methoxy]-piperidine, or a pharmaceutically acceptable salt thereof, is administered intravenously.

9. The method according to claim 1, wherein the effective amount of 4-[(2-naphthalenyl)-methoxy]-piperidine, or a pharmaceutically acceptable salt thereof, is administered topically in a formulation, said formulation comprising 4-[(2-naphthalenyl)-methoxy]-piperidine, or a pharmaceutically acceptable salt thereof, in combination with an absorption promoter.

10. The method according to claim 1, said method comprising administering to a subject having stress urinary incontinence an effective amount of 4-[(2-naphthalenyl)-methoxy]-piperidine, or a pharmaceutically acceptable salt thereof, in an amount between 0.001 and 1000 mg/day.

11. The method according to claim 1, said method comprising administering to a subject having mixed incontinence an effective amount of 4-[(2-naphthalenyl)-methoxy]-piperidine, or a pharmaceutically acceptable salt thereof, in an amount between 0.001 and 1000 mg/day.

12. The method according to claim 5, said method consisting of administering to a subject having stress urinary incontinence a formulation comprising an effective amount of 4-[(2-naphthalenyl)-methoxy]-piperidine, or a pharmaceutically acceptable salt thereof, in an amount between 0.001 and 1000 mg/day.

13. The method according to claim 5, said method consisting of administering to a subject having mixed incontinence a formulation comprising an effective amount of 4-[(2-naphthalenyl)-methoxy]-piperidine, or a pharmaceutically acceptable salt thereof, in an amount between 0.001 and 1000 mg/day.

* * * * *

UNITED STATES PATENT AND TRADEMARK OFFICE
CERTIFICATE OF CORRECTION

PATENT NO. : 9,511,061 B2  
APPLICATION NO. : 12/158444  
DATED : December 6, 2016  
INVENTOR(S) : Philippe Lluel et al.

Page 1 of 1

It is certified that error appears in the above-identified patent and that said Letters Patent is hereby corrected as shown below:

In the Specification

Column 4,
Line 46, "compounds 1-9" should read --compounds 1-49--.

Column 5,
Line 67, "($IC_{50\ NF/HT}$ ratio = 89)" should read --($IC_{50\ NE/HT}$ ratio = 89)--.

Column 14,
Line 35, "1155-1159," should read --II55-II59,--.

Signed and Sealed this  
Fourth Day of July, 2017

Joseph Matal  
*Performing the Functions and Duties of the*  
*Under Secretary of Commerce for Intellectual Property and*  
*Director of the United States Patent and Trademark Office*